(12) United States Patent
Chiwaki et al.

(10) Patent No.: US 7,994,348 B2
(45) Date of Patent: Aug. 9, 2011

(54) PROCESS FOR PRODUCING PROPYLENE OXIDE

(75) Inventors: Kenji Chiwaki, Chiba (JP); Kazuo Suzuki, Sodegaura (JP); Shigenori Shiraishi, Ichihara (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 494 days.

(21) Appl. No.: 11/997,159

(22) PCT Filed: Jul. 28, 2006

(86) PCT No.: PCT/JP2006/315436
§ 371 (c)(1),
(2), (4) Date: Feb. 6, 2008

(87) PCT Pub. No.: WO2007/015553
PCT Pub. Date: Feb. 8, 2007

(65) Prior Publication Data
US 2010/0094029 A1    Apr. 15, 2010

(30) Foreign Application Priority Data
Aug. 2, 2005   (JP) ................................. 2005-223772

(51) Int. Cl.
*C07D 301/19*    (2006.01)
*C07D 301/12*    (2006.01)
(52) U.S. Cl. ....................................... 549/531; 549/529
(58) Field of Classification Search .................. 549/529, 549/531
See application file for complete search history.

(56) References Cited

U.S. PATENT DOCUMENTS 5,993,673 A    11/1999    Evans et al.

FOREIGN PATENT DOCUMENTS

| JP | 2-268174 A    | 11/1990 |
| JP | 8-104682 A    | 4/1996  |
| JP | 10-045737 A   | 2/1998  |
| JP | 10-306086 A   | 11/1998 |
| JP | 2000-107605 A | 4/2000  |
| JP | 2001-031662 A | 2/2001  |
| JP | 2001-270875 A | 10/2001 |
| JP | 2001-270876 A | 10/2001 |
| JP | 2003-160573 A | 6/2003  |
| JP | 2004-285056 A | 10/2004 |
| JP | 2005-097183 A | 4/2005  |
| JP | 2005-097184 A | 4/2005  |

OTHER PUBLICATIONS

Tsuji et al., JP 2005-097184, Apr. 4, 2005, Translation.*
Tsuji et al., JP 2005-097183, Apr. 4, 2005, Translation.*
Tsuji et al., JP 2001-270876, Oct. 2, 2001, Translation.*
Tsuji et al., JP 2001-270875, Oct. 2, 2001, Translation.*
Oku et al., JP 2001-031662, Feb. 6, 2001, Translation.*

* cited by examiner

*Primary Examiner* — Taylor Victor Oh
(74) *Attorney, Agent, or Firm* — Sughrue Mion, PLLC

(57) ABSTRACT

A process for producing propylene oxide, which comprises:
supplying a solution containing a peroxide selected from the group consisting of hydrogen peroxide and organic hydroperoxide having 2 or more of carbon atoms as a raw material and propylene to an epoxidation step to react the peroxide with propylene, and
controlling a concentration of methyl hydroperoxide in the solution to be supplied to the epoxidation step.

5 Claims, No Drawings

PROCESS FOR PRODUCING PROPYLENE OXIDE

TECHNICAL FIELD

The present invention relates to a process for producing propylene oxide. More particularly, the present invention relates to a process for producing propylene oxide in which formation of methyl alcohol as an impurity can be effectively reduced in a step for obtaining propylene oxide by reacting a peroxide selected from the group consisting of hydrogen peroxide and organic hydroperoxides having 2 or more of carbon atoms with propylene.

BACKGROUND ART

In a process for obtaining propylene oxide by oxidizing propylene using a peroxide as an oxygen carrier, use of hydrogen peroxide, peracetic acid, ethylbenzene hydroperoxide, cumene hydroperoxide, t-butyl hydroperoxide or the like, is known (e.g. Kagaku Binran (third revision) (edit. by the Japan Chemical Society, pages 610-612). Since various impurities are contained in crude propylene oxide obtained by the above process in addition propylene oxide as a target product, a purification step for removing the impurities is required. For example, as the impurities, methyl alcohol is listed as a hardly separable component, in addition to light components such as hydrocarbons and heavy components such as acetone. Though the concentration of methyl alcohol contained in crude propylene oxide to be subjected to a propylene oxide purification step, is an important factor for quality control of propylene oxide as a product, there has not been any effective index for controlling the concentration of methyl alcohol. Therefore, further improvement has been required because of a variation in the quality of propylene oxide as a product caused by a frequent fluctuation of a load for methyl alcohol removal in the purification step.

DISCLOSURE OF THE INVENTION

Under such situations, the present inventors found that the methyl alcohol concentration in crude propylene oxide obtained in production of propylene oxide through reaction of a peroxide selected from the group consisting of hydrogen peroxide and organic hydroperoxides having 2 or more of carbon atoms with propylene, or in purified propylene oxide, can be controlled by controlling the concentration of methyl hydroperoxide contained in a solution containing a peroxide as a raw material to be supplied to an epoxidation step, then completed the invention.

Herein, crude propylene oxide is obtained by removing unreacted propylene, the corresponding alcohol produced and a solvent by distillation from a reaction mixture obtained in the epoxidation step.

An object of the invention is to provide a process for producing propylene oxide, which comprises supplying a solution containing a peroxide selected from the group consisting of hydrogen peroxide and organic hydroperoxides having 2 or more of carbon atoms as a raw material and propylene to an epoxidation step to react the peroxide with propylene, and reducing the variation in a load for methyl alcohol removal in the purification step, and controlling an amount of methyl alcohol to lower level.

Namely, the present invention relates to a process for producing propylene oxide, which comprises:

supplying a solution containing a peroxide selected from the group consisting of hydrogen peroxide and organic hydroperoxides having 2 or more of carbon atoms as a raw material and propylene to an epoxidation step to react the peroxide with propylene, and controlling a concentration of methyl hydroperoxide in the solution to be supplied to the epoxidation step to control the methyl alcohol concentration in crude propylene oxide.

Further, the present invention relates to a process for producing propylene oxide, which comprises supplying a solution containing a peroxide selected from the group consisting of hydrogen peroxide and organic hydroperoxide having 2 or more of carbon atoms and propylene to an epoxidation step to react the peroxide with propylene, wherein a concentration of methyl hydroperoxide in the solution to be supplied to the epoxidation step is from 0.1 ppm to 100 ppm by weight.

BEST MODE FOR CARRYING OUT THE INVENTION

As the peroxides to be reacted with propylene, hydrogen peroxide and organic hydroperoxides having 2 or more of carbon atoms are preferably used, and among these cumene hydroperoxide is more preferable.

As an Example, a process for producing propylene oxide using cumene hydroperoxide as the peroxide (cumene method) is mainly explained in detail below.

The cumene method contains:

an oxidation step of obtaining cumene hydroperoxide by oxidizing cumene;

an epoxidation step of obtaining propylene oxide and cumyl alcohol by reacting cumene hydroperoxide obtained in the oxidation step with propylene in the presence of a solid catalyst;

a step of converting cumyl alcohol obtained in the epoxidation step into cumene by subjecting cumyl alcohol to dehydration-hydrogenation or hydrogenolysis, and recycling the cumene obtained to the oxidation step; and a purification step of obtaining purified propylene oxide as a product by purifying crude propylene oxide in which unreacted propylene, cumyl alcohol and cumene are removed from a reaction mixture obtained in the epoxidation step by distillation.

A solution containing cumene hydroperoxide obtained in the oxidation step also contains unreacted cumene (operating as a solvent), and acetophenone, cumyl alcohol, water and methyl hydroperoxide and the like as impurities. A solution containing cumene hydroperoxide produced in oxidation step is supplied to the epoxidation step after controlling methyl hydroperoxide concentration. As control method, washing with water and/or distillation are listed. Method of washing with water include that after mixing of the solution with water, the mixture is separated into a water (aqueous) phase and oil phase, then the water phase is removed (these operations may be repeated two or more times). Ratio of the volume of the solution and water (o/w) is normally 100/1 to 1/1 and 20/1 to 1/1 is preferable. If o/w is too large, it is impossible to control methyl hydroperoxide concentration in the solution after removed water phase, and if o/w is too small, water phase removed become too large. The temperature of washing with water is normally 0 to 95° C. and 20-75° C. is preferable. If the temperature is too high, There is a possibility of increasing unfavorable side reactions of cumene hydroperoxide like heat decomposition. And if the temperature is too low, it is not economical because of too much energy to cool the solution.

As washing method, both batch and continuous operation are available. It is possible to reuse removed water phase by mixing with fresh water as washing water.

As distillation column, packed tower and plate tower are available, but are not limited to. Operation condition of distillation column is not limited, but normally the temperature of the top of the column is 30 to 150° C., the pressure of the top of the column is −100 to 500 kPaG, the temperature of the bottom of the column is 30 to 150° C., and the pressure of the bottom of the column is −100 to 500 kPaG.

A solution containing cumene hydroperoxide controlled the concentration of methyl hydroperoxide by the methods mentioned above is preferably analyzed the concentration of methyl hydroperoxide by means of liquid chromatography and, if necessary, controlled the methyl hydroperoxide concentration by repeating the above-washing operation or increasing the plate number in the distillation column or changing the condition of distillation column. If too much methyl hydroperoxide remains in a solution containing cumene hydroperoxide, too much cost is required at the purification step. On the other hand, too much cost for the operation of washing step and/or distillation step is required to control methyl hydroperoxide concentration in a solution containing cumene hydroperoxide to 0.1 ppm or less. Therefore, it is preferable to control the concentration of methyl hydroperoxide to 0.1 to 100 ppm, more preferably 0.1 to 50 ppm, most preferably 1 to 20 ppm.

In purification step, elimination of light components such as hydrocarbons, heavy components such as acetone, and methyl alcohol and the like, is carried out. Particularly, the methyl alcohol concentration in propylene oxide as a product, is required to reduce depending on users demand. However, elimination of methyl alcohol is difficult in a usual distillation operation, therefore, it is required to use means of an extractive distillation or the like, further, a large load, for example, increase of theoretical plate numbers in the extractive distillation, addition of a distillation column and the like become necessary. Methods of extractive distillation are described in JP 2001-302649 A, JP 2003-238548 A and JP 2005-281163 A.

On the other hand, according to the present invention, in such the case, the concentration of methyl alcohol contained in crude propylene oxide can be considerably reduced by controlling the methyl hydroperoxide concentration in the solution containing the peroxide such as cumene hydroperoxide to 0.1 to 100 ppm, more preferably 0.1 to 50 ppm, most preferably 1 to 20 ppm, thereby reducing the purification load for methyl alcohol in the extractive distillation to a large extent. Namely, according to the present invention, it is possible to efficiently produce propylene oxide containing methyl alcohol in a small amount compared to conventional methods.

EXAMPLE

The present invention is described in detail by Examples below.

Example 1

Various solutions (raw material for epoxidation) containing cumene as a solvent having methyl hydroperoxide (MPO) concentrations (measured by liquid chromatography method) shown in Table 1 were obtained by subjecting to water-washing and distillation under various conditions of a cumene solution of cumene hydroperoxide containing 110 ppm of MPO obtained by oxidation of cumene, respectively.

Each of those solutions was subjected to epoxidation with propylene to obtain propylene oxide (60 to 150° C. as operation temperature and 5.0 to 7.0 kPaG as operation pressure).

Thus obtained reaction mixture was distilled to remove unreacted propylene, subsequently distilled for obtaining crude propylene oxide by removing cumene and cumyl alcohol.

The concentration of methyl alcohol (MeOH) in each crude propylene oxide was measured by a gas chromatography method, and shown in Table 1.

The crude propylene oxide was further purified by a conventional purification method using rectification columns containing publicly known extractive distillation for obtaining a purified propylene oxide having a methyl alcohol concentration shown in Table 1.

From results shown in Table 1, the followings are found.

There is a correlation ship between the concentration of methyl hydroperoxide in the raw material for epoxidation and the concentration of methyl alcohol in crude propylene oxide or purified propylene oxide.

TABLE 1

| MPO concentration in raw material for epoxidation (ppm by weight) | MeOH concentration in crude propylene oxide (ppm by weight) | MeOH concentration in purified propylene oxide (ppm by weight) |
| --- | --- | --- |
| 7.5 | 132 | 4.8 |
| 8.5 | 151 | 5.6 |
| 10.0 | 252 | 7.4 |
| 34.0 | 436 | 11.8 |

Industrial Applicability

According to the present invention, there can be provided a process for producing propylene oxide, which can control an amount of methyl alcohol by controlling an amount of methyl hydroperoxide contained in the solution containing of a peroxide as a raw material to be supplied to the epoxidation step, and which can control a load of methyl alcohol for purification to lower level because the concentration of methyl alcohol in which separation is difficult, can be efficiently suppressed to lower level by controlling the concentration of methyl hydroperoxide of the solution as the raw material to lower level.

The invention claimed is:

1. A process for producing propylene oxide, which comprises:
    supplying a solution containing a peroxide selected from the group consisting of hydrogen peroxide and organic hydroperoxide having 2 or more of carbon atoms as a raw material and propylene to an epoxidation step to react the peroxide with propylene, and
    controlling a concentration of methyl hydroperoxide in the solution to be supplied to the epoxidation step to be 1 to 20 ppm by weight.

2. The process according to claim 1, wherein the solution containing a peroxide selected from the group consisting of hydrogen peroxide and organic hydroperoxide having 2 or more of carbon atoms as a raw material is washed with water and/or distillated to control the methyl hydroperoxide concentration in the solution.

3. The process according to claim 1, wherein the peroxide is the organic peroxide having 2 or more of carbon atoms.

4. The process according to claim 3, the organic peroxide having 2 or more of carbon atoms is cumene hydroperoxide.

5. The process according to claim 4, wherein cumene hydroperoxide is produced by oxidation of cumene.

* * * * *